(12) United States Patent
Langbein et al.

(10) Patent No.: US 9,128,059 B2
(45) Date of Patent: Sep. 8, 2015

(54) COHERENT ANTI-STOKES RAMAN SPECTROSCOPY

(75) Inventors: Wolfgang Langbein, Cardiff South Glamorgan (GB); Paola Borri, Cardiff South Glamorgan (GB)

(73) Assignee: University College Cardiff Consultants Ltd. (GB)

( * ) Notice: Subject to any disclaimer, the term of this patent is extended or adjusted under 35 U.S.C. 154(b) by 773 days.

(21) Appl. No.: 13/257,194

(22) PCT Filed: Mar. 19, 2010

(86) PCT No.: PCT/GB2010/050473
§ 371 (c)(1),
(2), (4) Date: Dec. 22, 2011

(87) PCT Pub. No.: WO2010/106376
PCT Pub. Date: Sep. 23, 2010

(65) Prior Publication Data
US 2012/0092662 A1 Apr. 19, 2012

(30) Foreign Application Priority Data
Mar. 19, 2009 (GB) .................................. 0904739.0

(51) Int. Cl.
*G01J 3/44* (2006.01)
*G01J 3/30* (2006.01)
(Continued)

(52) U.S. Cl.
CPC . *G01N 21/65* (2013.01); *G01J 3/02* (2013.01); *G01J 3/0224* (2013.01); *G01J 3/44* (2013.01); *G01N 2021/653* (2013.01)

(58) Field of Classification Search
CPC ............................................... G01N 2021/653
USPC ................. 356/301, 317–318, 417; 250/458.1–461.2; 422/82.07–82.08
See application file for complete search history.

(56) References Cited

U.S. PATENT DOCUMENTS

| 7,403,282 B2 | 7/2008 | Silberberg et al. |
| 2004/0145735 A1 | 7/2004 | Silberberg et al. |

(Continued)

FOREIGN PATENT DOCUMENTS

| EP | 1588152 B1 | 5/2008 |
| WO | 2004068126 A1 | 8/2004 |
| WO | 2005116596 A1 | 12/2005 |

OTHER PUBLICATIONS

Jones et al., "High-spectral-resolution coherent anti-Stokes Raman scattering with interferometrically detected broadband chirped pulses", Optics Letters, May 15, 2006, vol. 31, No. 10, pp. 1543-1545, Optical Society of America.

(Continued)

*Primary Examiner* — Tarifur Chowdhury
*Assistant Examiner* — Sunghee Y Gray
(74) *Attorney, Agent, or Firm* — Fitch, Even, Tabin & Flannery, LLP

(57) ABSTRACT

A coherent anti-Stokes Raman spectroscopy (CARS) system comprises a laser light source for emitting pulsed light, a dichroic beam splitter for splitting a light pulse from the light source into a pump pulse and a Stokes pulse and directing these pulses along respective distinct paths, chirping means, e.g. dispersive glass blocks for chirping the pump and Stokes pulses, directing means for directing the chirped pump and Stokes samples to a sample in time overlap, and detecting means for detecting light stimulated from the sample by the interaction of the pump and Stokes pulses. The system may comprise a reflector connected to a linear motor, for adjusting the period between the arrival at the sample of the starts of the chirped pump and Stokes pulses. The system may further comprise a pulse replicating unit for converting a pulse from the light source into a plurality of pulses distributed in time.

14 Claims, 12 Drawing Sheets

(51) Int. Cl.
G01N 21/25 (2006.01)
G01J 1/58 (2006.01)
G01N 21/64 (2006.01)
G01N 21/65 (2006.01)
G01J 3/02 (2006.01)

(56) References Cited

U.S. PATENT DOCUMENTS

| | | | |
|---|---|---|---|
| 2006/0192969 A1* | 8/2006 | Marks et al. | 356/451 |
| 2007/0258088 A1 | 11/2007 | Silberberg et al. | |
| 2007/0291264 A1 | 12/2007 | Silberberg et al. | |
| 2008/0059135 A1* | 3/2008 | Murugkar et al. | 703/11 |
| 2008/0291443 A1 | 11/2008 | Malinovskaya et al. | |
| 2011/0273768 A1* | 11/2011 | Krishnamachari et al. | 359/388 |

OTHER PUBLICATIONS

Lepetit et al., "Linear techniques of phase measurement by femtosecond spectral interferometry for applications in spectroscopy", Journal of Optical Society of Am. B., Dec. 1995, vol. 12, No. 12, pp. 2467-2474, Optical Society of America.

Potma et al., "Detection of single lipid bilayers with coherent anti-stokes raman scattering (CARS) microscopy", Journal of Raman Spectroscopy, 2003, vol. 34, pp. 642-650, Wiley InterScience.

Vacano et al., "Time-resolving molecular vibration for microanalytics: single laser beam nonlinear Raman spectroscopy in simulation and experiment", Phys. Chem. Chem. Phys., 2008, vol. 10, No. 5, pp. 681-691, RSC Publishing.

Burkacky et al., "Dual-pump coherent anti-Stokes-Raman scattering microscopy", Optics Letters, Dec. 15, 2006, vol. 31, No. 24, pp. 3656-3658, Optical Society of America.

Ganikhanov et al., "High-sensitivity vibrational imaging with frequency modulation coherent anti-Stokes Raman scattering (FM CARS) microscopy", Optical Letters, Jun. 15, 2006, vol. 31, No. 12, pp. 1872-1874, Optical Society of Am.

Haim Lotem, "Frequency modulation coherent anti-Stokes Raman spectroscopy (FM-CARS): a novel sensitive nonlinear optical method", Journal of Chem. Phys., Sep. 1, 1983, vol. 79, No. 5, pp. 2177-2180, American Institute of Physics.

Lu et al., "Heterodyne polarization coherent anti-Stokes Raman scattering microscopy", Applied Physics Letters, 2008, vol. 92, pp. 123901-1-123901-3, American Institute of Physics.

Lu et al., "Interferometric polarization coherent anti-Stokes Raman scattering (IP-CARS) microscopy", Optics Letters, Mar. 15, 2008, vol. 33, No. 6, pp. 602-604, Optical Society of America.

Yoo et al., "Differential two-signal picosecond-pulse coherent anti-Stokes Raman scattering imaging microscopy by using a dual-mode optical parametric oscillator", Optics Letters, Nov. 15, 2007, vol. 32, No. 22, pp. 3254-3256, Optical Society of America.

McCamant et al., Femtosecond broadband stimulated Raman spectroscopy: apparatus and methods, Review of Scientific Instruments, Nov. 2004, vol. 75, No. 11, pp. 4971-4980, American Institute of Physics.

Cheng et al., "Multiplex coherent anti-Stokes Raman scattering microspectroscopy and study of lipid vesicles", J. Phys. Chem. B., 2002, vol. 106, pp. 8493-8498, American Chemical Society.

Jiang et al., "Nonlinear interferometric vibrational imaging of biological tissue", Proc. of SPIE, Jan. 2008, vol. 6860, pp. 68600-68601.

Kano et al., "Three-dimensional vibrational imaging of a microcrystalline j-aggregate using supercontinuum-based ultrabroadband multiplex coherent anti-Stokes Raman scattering microscopy", J. Phys. Chem. B., 2006, vol. 110, pp. 3120-3126, American Chemical Society.

Kano et al., "Dispersion-compensated supercontinuum generation for ultraboardband multiplex coherent anti-Stokes Raman scattering spectroscopy", Journal of Raman Spectroscopy, 2006, vol. 37, pp. 411-415, Wiley InterScience.

Kee et al., "Simple approach to one-laser, broadband coherent anti-Stokes Raman scattering microscopy", Optics Letters, Dec. 1, 2004, vol. 29, No. 23, pp. 2701-2703, Optical Society of America.

Knutsen et al., "High spectral resolution multiplex CARS spectroscopy using chirped pulses", Chemical Physics Letters, 2004, vol. 387, pp. 436-441, Elseview B.V.

Knutsen et al., "Chirped coherent anti-Stokes Raman scattering for high spectral resolution spectroscopy and chemically selective imaging", J. Phys. Chem. B., 2006, vol. 110, pp. 5854-5864, American Chem. Society.

Lim et al., "Single-pulse phase-control interferometric coherent anti-Stokes Raman scattering spectroscopy", Physical Review A, 2005, vol. 72, pp. 041803-1-041803-4, The American Physical Society.

Onorato et al., "Chirped coherent anti-Stokes Raman scattering as a high-spectral- and spatial-resolution microscopy", Optics Letters, Oct. 1, 2007, vol. 32, No. 19, pp. 2858-2860, Optical Society of America.

Porter et al., "Coherent anti-Stokes Raman scattering microscopy with spectrally tailored ultrafast pulses", Review of Scientific Instruments, 2005, vol. 76, pp. 043108-1-043108-5, American Institute of Physics.

Potma et al., "Heterodyne coherent anti-Stokes Raman scattering (CARS) imaging", Optics Letters, vol. 31, No. 2, Jan. 15, 2006, pp. 241-243, Optical Society of America.

Urbanek et al., "Simultaneous time and frequency detection in femtosecond coherent Raman spectroscopy. I. Theory and model calculations", The Journal of Chemical Physics, 2007, vol. 127, pp. 044306-1-044306-10, American Institute of Physics.

Yoon et al., "Dependence of line shapes in femtosecond broadband stimulated Raman spectroscopy on pump-probe time delay", The Journal of Chemical Physics, 2005, vol. 122, pp. 024505-1-024505-9, American Institute of Physics.

Cheng et al., "Coherent anti-Stokes Raman scattering microscopy: instrumentation, theory, and applications", J. Phys. Chem. B., 2004, vol. 108, pp. 827-840, American Chemical Society.

Müller et al., "Coherent anti-Stokes Raman scattering (CARS) microscopy", ChemPhysChem, 2007, vol. 8, pp. 2156-2170, Wiley InterScience.

Potma et al., "CARS microscopy for biology and medicine", Optics & Photonics New, Nov. 2004, pp. 40-45, Optical Society of America.

Andreas Volkmer, "Vibrational imaging and microspectroscopies based on coherent anti-Stokes Raman scattering microscopy", J. Phys. D: Appl. Phys., 2005, vol. 38, pp. R59-R81, IOP Publishing Ltd., UK.

Cui et al., "interferometric Fourier transform coherent anti-stokes raman scattering", Optics Express, Sep. 4, 2006, vol. 14, No. 18, pp. 8448-8458, OSA.

Dudovich et al., "Single-pulse coherently controlled nonlinear Raman spectroscopy and microscopy", Nature, Aug. 2002, vol. 418, pp. 512-514, Nature Publishing Group.

Kee et al., "One-laser interferometric broadband coherent anti-Stokes Raman scattering", Optics Express, Apr. 17, 2006, vol. 14, No. 8, pp. 3631-3640, OSA.

Lee et al., "Vibrational dephasing time imaging by time-resolved broadband coherent anti-Stokes Raman scattering microscopy", Applied Physics Letters, 2008, vol. 92, pp. 041108-1-041108-3, American Institute of Physics.

Lim et al., "Chemical imaging by single pulse interferometric coherent anti-stokes raman scattering microscopy", J. Phys. Chem. B., 2006, vol. 110, No. 11, pp. 5196-5204, ACS Publications.

Lim et al., "Fourier transform spectral interferometric coherent anti-Stokes Raman scattering (FTSI-CARS) spectroscopy", Optics Letters, May 15, 2007, vol. 32, No. 10, pp. 1332-1334, Optical Society of America.

Nath et al., "High-resolution Raman spectra with femtosecond pulses: an example of combined time- and frequency-doman spectroscopy", Physical Review Letters, Dec. 31, 2006, PRL97, pp. 267401-1-267401-4, The American Physical Society.

Ogilvie et al., "Fourier-transform coherent anti-Stokes Raman scattering microscopy", Optics Letters, Feb. 15, 2006, vol. 31, No. 4, pp. 480-482, Optical Society of America.

Gershgoren et al., "Simplified setup for high-resolution spectroscopy that uses ultrashort pulses", Optics Letters, Mar. 1, 2003, vol. 28, No. 5, pp. 361-363, Optical Society of America.

(56) References Cited

OTHER PUBLICATIONS

Nibbering et al., "Ultrafast nonlinear spectroscopy with chirped optical pulses", Physical Review Letters, Jan. 27, 1992, vol. 68, No. 4, pp. 514-518, The American Physical Society.

Pestov et al., "Pulse shaping for mode-selective ultrafast coherent Raman spectroscopy of highly scattering solids", J. Opt. Soc. Am. B, May 2008, vol. 25, No. 5, pp. 768-772, Optical Society of America.

Weling et al., "Generation of tunable narrow-band THz radiation from large aperture photoconducting antennas", Appl. Phys. Lett., Jan. 10, 1994, vol. 64, No. 2, pp. 137-139, American Institute of Physics.

Yellampalle et al., "Spectral interferometric coherent Raman imaging", Optics Express, Sep. 19, 2005, vol. 13, No. 19, pp. 7672-7682, OSA.

Vacano et al., "Rapid polymer blend imaging with quantitative broadband multiplex CARS microscopy", Journal of Raman Spectroscopy, 2007, vol. 38, pp. 916-926, Wiley InterScience.

Xu et al., "Background-free coherent Raman spectroscopy by detecting the spectral phase of molecular vibrations", Optics Letters, Jun. 1, 2008, vol. 33, No. 11, pp. 1177-1179, Optical Society of America.

I. Rocha-Mendoza et al., "Coherent anti-Stokes Raman microspectroscopy using spectral focusing with glass dispersion", Applied Physics Letters, vol. 93, 201103, 2008.

T. Hellerer et al., "Highly efficient coherent anti-Stokes Raman scattering (CARS)-microscopy", Proc. of SPIE, vol. 5323, 2004, pp. 223-229.

A.F. Pegoraro et al., "High performance multimodal CARS microscopy using a single femtosecond source", Proc. of SPIE, vol. 7183, 2009, pp. 71830Z-1-71830Z-9.

I. Rocha-Mendoza et al., "CARS Microscopy using linearly-chirped ultrafast laser pulses", Proc. of SPIE, vol. 7183, 2009, pp. 71830T-1-71830T-9.

Pegoraro A. et al., "Optimally chirped multimodal CARS microscopy based on a single Ti:sapphire oscillator" Optics Eexpress, vol. 17, No. 4, Feb. 16, 2009, pp. 2984-2996.

Hellerer T. et al., "Spectral focusing: High spectral resolution spectroscopy with broad-bandwidth laser pulses", Applied Physics Letters, AIP, American Institute of Physics, Melville, NY, US, LNKD, vol. 85, No. 1, Jan. 1, 2004, pp. 25-27.

Langbein W. et al., "Single source coherent anti-Stokes Raman microspectroscopy using spectral focusing", Applied Physics Letters, AIP, American Institute of Physics, Melville, NY, US, vol. 95, No. 8, Aug. 27, 2009, pp. 81109-1-81109-3.

Rocha-Mendoza, I. et al., "Differential coherent anti-Stoke Raman scattering microscopy with linearly chirped femtosecond laser pulses", Optics Letters, OSA, Optical Society of America, Washington, DC, US, vol. 34, No. 15, Aug. 1, 2009, pp. 2258-2260.

International Search Report for PCT/GB2010/050473 issued on Jun. 30, 2010.

Search Report for GB0904739.0 of Dec. 16, 2009.

\* cited by examiner

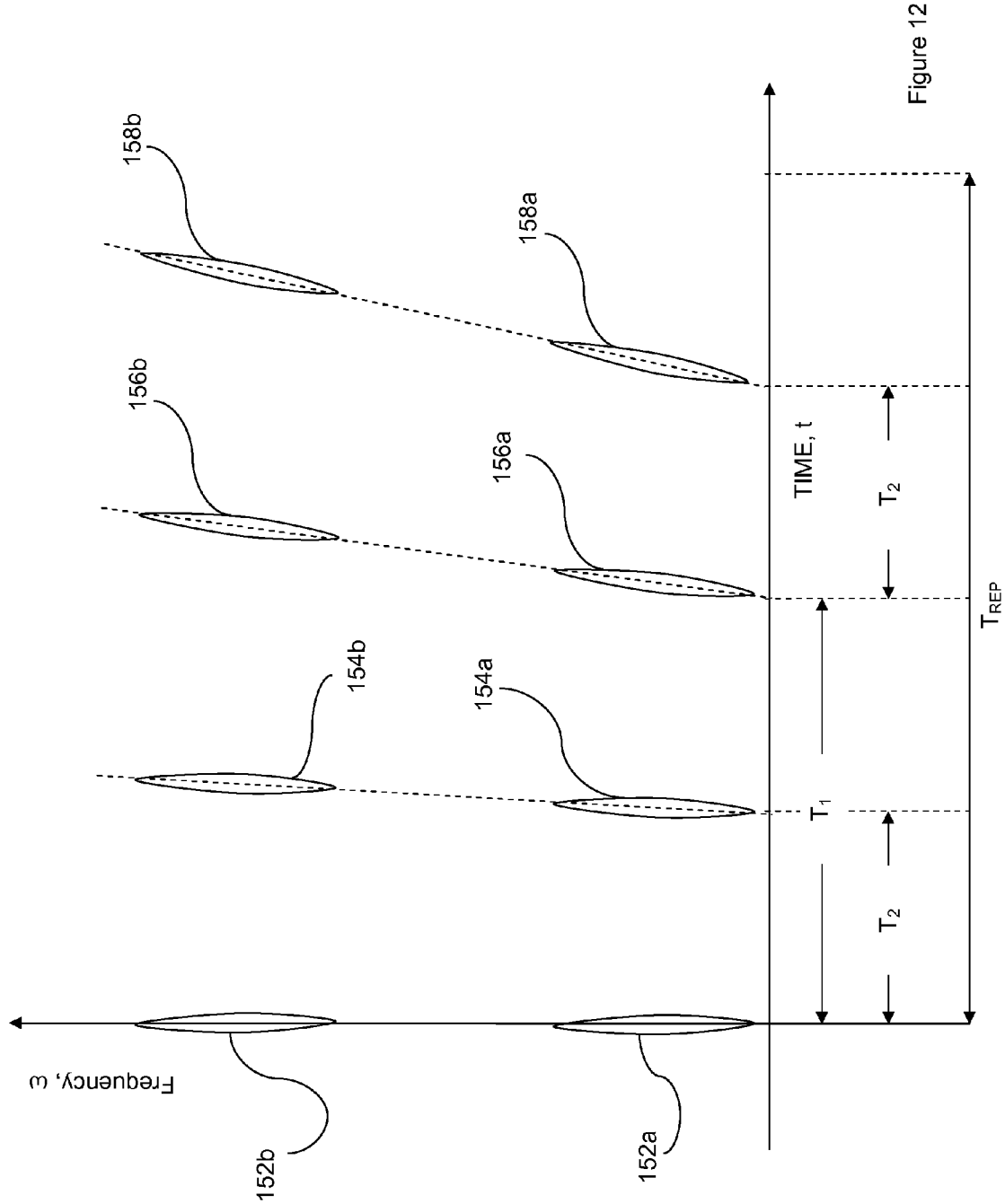

COHERENT ANTI-STOKES RAMAN SPECTROSCOPY

CROSS REFERENCE TO RELATED APPLICATIONS

This application is a national phase application of International Application No. PCT/GB2010/050473, filed Mar. 19, 2010, claiming priority to Great Britain Application No. 0904739.0, filed Mar. 19, 2009, both of which are incorporated by reference herein in their entirety.

FIELD

The invention relates to the field of probing material with electromagnetic radiation to acquire information about the material.

BACKGROUND

Coherent anti-Stokes Raman spectroscopy (CARS) is a known technique for investigating the properties of materials such as biological cells. In a typical CARS system, a sample is illuminated with a pump beam and a Stokes beam and responds by emitting anti-Stokes radiation. A brief, classical (as opposed to quantum-mechanical) description of the physics of CARS will now be given.

Consider a molecule having a vibrational mode with a resonant frequency of $\omega_v$. If the frequencies of the pump beam $\omega_p$ and the Stokes beam $\omega_s$ are such that $\omega_p - \omega_s = \omega_v$, then the molecule will respond by emitting radiation forming a CARS beam at frequency $\omega_c = \omega_p + \omega_v$ that can then be detected.

Existing CARS systems utilise separate pulsed lasers to provide the pump and Stokes beams. These beams must be aligned optically and made incident upon the same volume within the target sample and the pulses from the two lasers must arrive at that volume at the same time. CARS systems of this type require expert attention in order to achieve the aforementioned spatial and temporal alignment of the delivery of the laser radiation and are often fragile in that this alignment can easily be upset (e.g., by physical shock). However, it is known to use a single laser source to provide both the pump and Stokes beams, as reported in for example in Physical Chemistry Chemical Physics 10, 609 (2008) and the documents referenced therein.

In order to target a vibrational mode of interest within a sample under analysis that has a resonant frequency $\omega_v$, the pump and Stokes beams must be tuned accurately to achieve $\omega_p - \omega_s = \omega_v$. Typically, this tuning is achieved by using diffraction gratings and liquid crystal arrays or similar to select desired probed CARS frequencies from broadband laser emissions. Again, such tuning arrangements can be awkward and sensitive to disruption.

SUMMARY

The invention relates to Coherent anti-Stokes Raman spectroscopy (CARS). A single light source may be used to generate pump and Stokes beams of interrogating light. Pump and Stokes beams may be chirped in various ways to produce various effects in the CARS light that is produced. Components of pulses of interrogation light may be delayed relative to others to allow multiple investigations to be performed in the same apparatus. Fourier analysis may be used to derive differential results from the multiple investigations. The invention is defined in the appended claims to which reference should now be made.

BRIEF DESCRIPTION OF THE DRAWINGS

By way of example only, certain embodiments of the invention will now be described by reference to the accompanying drawings, in which:

FIG. 12 is a graph illustrating the effect of the pulse replicating unit of FIG. 10.

DETAILED DESCRIPTION

Figure 1:
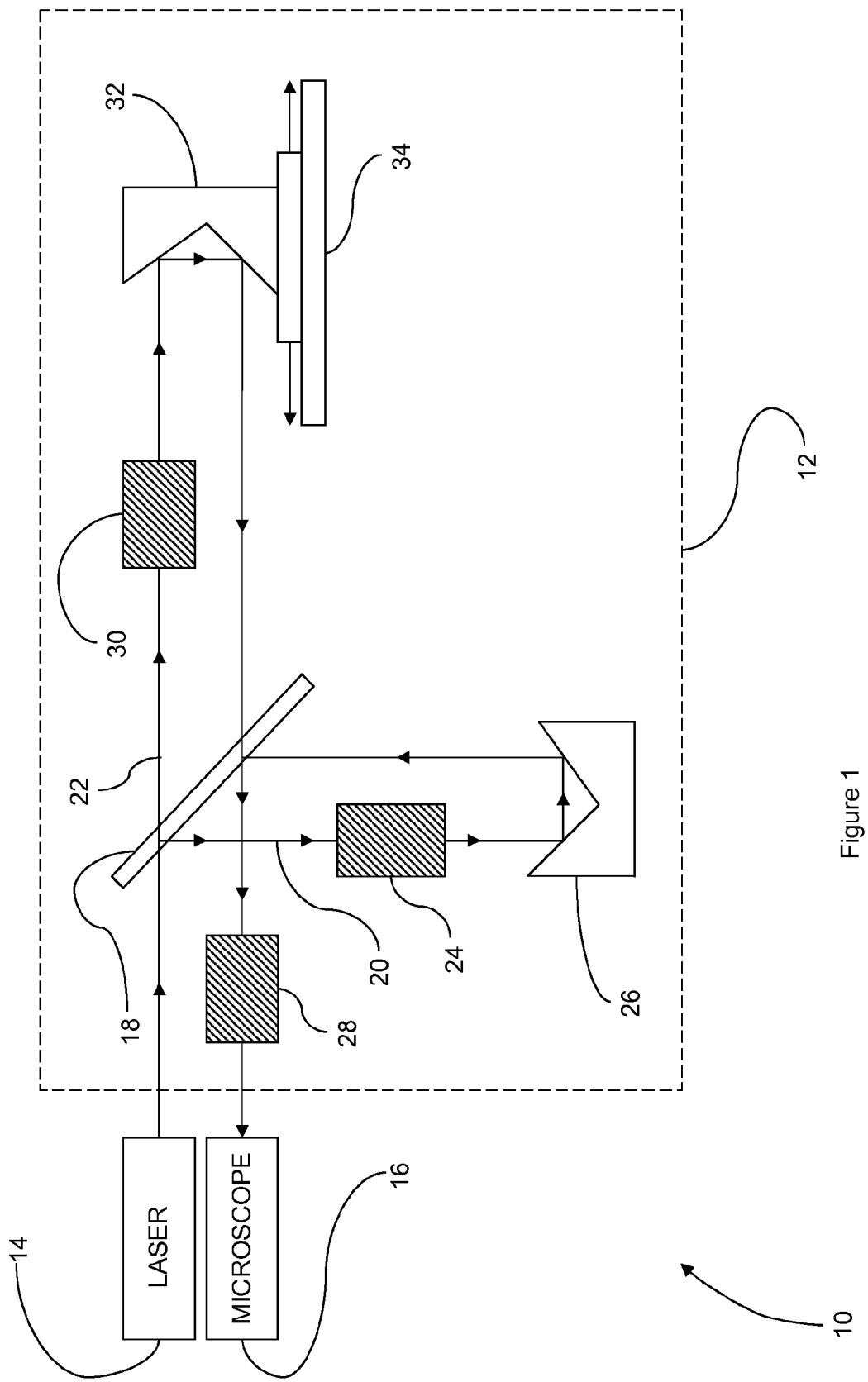
FIG. 1 is a block diagram schematically illustrating a CARS system.

FIG. 1 illustrates a CARS system 10 that comprises a chirp unit 12 that modifies broadband light from a laser 14 to create interrogation light that is delivered to a microscope 16 to stimulate a target sample (not shown) within the microscope 16 to emit CARS light. The laser 14 emits linearly polarised light in pulses of duration of less than 10 fs and consisting of broadband light covering a wavelength range of 700 to 950 nm. The microscope 16 is a standard confocal fluorescence microscope. The nature of the chirp unit 12 will now be discussed.

In the chirp unit 12, light from the laser is incident upon a dichroic beam splitter 18 that splits the laser light into two beams 20 and 22, each containing a different sub-band of the frequencies contained in the laser emissions. Beam 20 shall be called the Stokes beam and beam 22 shall be called the pump beam. From the dichroic beam splitter 18, the Stokes beam 20 passes through a dispersive glass block 24, reflects from a retroreflector 26 of corner cube type, reflects again from the dichroic beam splitter 18, passes through a further dispersive glass block 28 and enters the microscope 16. From the dichroic beam splitter 18, the pump beam 22 passes through a dispersive glass block 30, reflects from a retroreflector 32 of corner cube type, passes through the dichroic beam splitter 18, passes through the dispersive glass block 28 and enters the microscope 16. The dichroic beam splitter 18 is positioned such that the pump and Stokes beams 22 and 24 enter the microscope 16 along the same optical path.

The retroreflector 32 is mounted on a linear motor 34. The motor 34 can move the retroreflector 32 back and forth along the optical path from the laser 14 to lengthen or shorten the travel time from the laser 14 to the microscope 16 of a pulse in the pump beam 22. The glass blocks 24, 28 and 30 cause dispersion in the laser pulses. That is to say, they delay the different frequencies of the laser pulses by different amounts of time. The amount of dispersion that the blocks 24, 28 and 30 are designed to cause will shortly be described.

Figure 3:
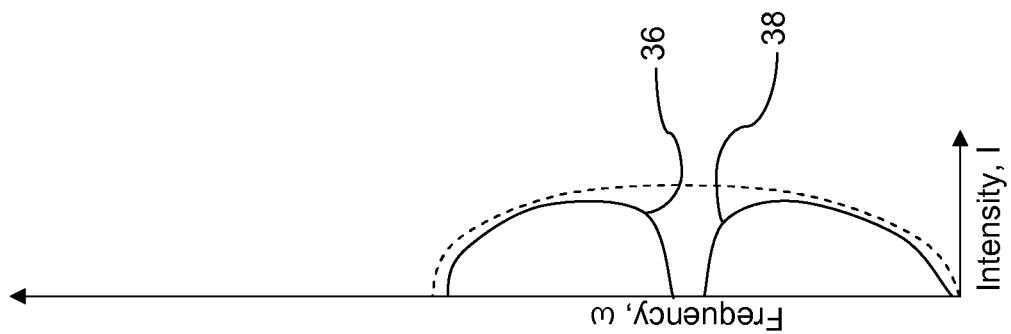
FIG. 3 is a graph of intensity versus frequency for the laser in the CARS system of FIG. 1 after filtering has been applied.
Figure 2:
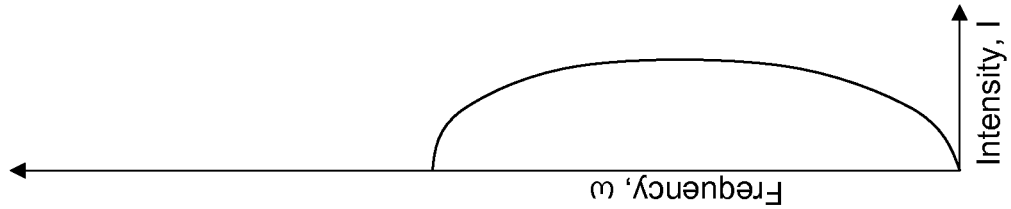
FIG. 2 is a graph of intensity versus frequency for the broadband laser used in the CARS system of FIG. 1.

FIG. 2 illustrates the spectrum of a pulse from the laser 14 and FIG. 3 illustrates the filtering effect of the dichroic beam splitter 18. In FIG. 3, the spectrum of FIG. 2 is overlaid as a dashed outline for comparison purposes and the spectra of the Stokes and pump beams 20 and 22 are indicated 38 and 36, respectively. A laser pulse that passes through the dichroic beam splitter 18 is divided into a "Stokes pulse" and a "pump pulse". The Stokes pulse is the part of the laser pulse that has spectrum 38 and forms part of the Stokes beam 20. The pump pulse is the part of the laser pulse that has spectrum 36 and forms part of the pump beam 22.

Figure 4:
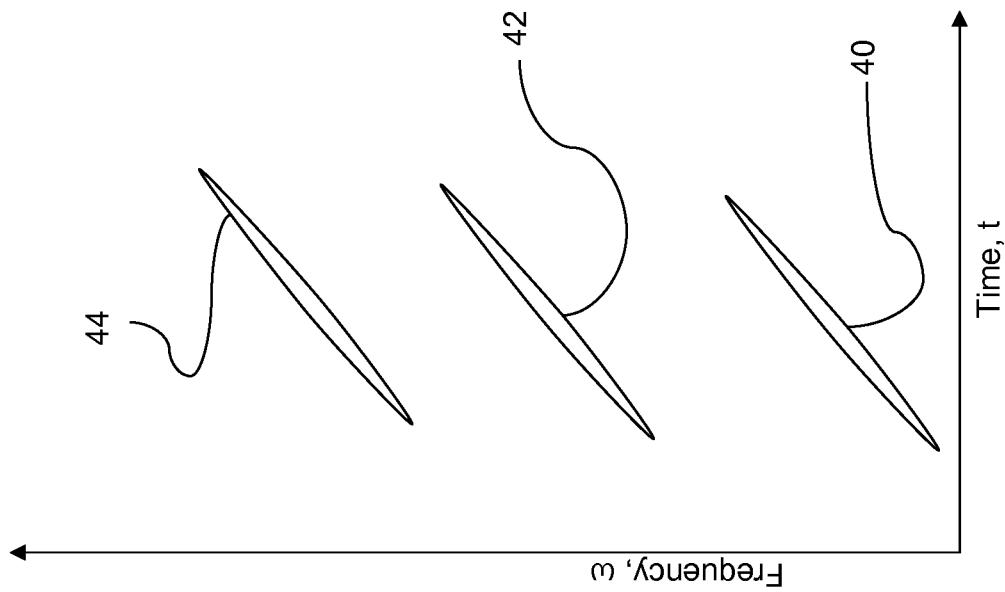
FIG. 4 is a graph of frequency versus time for various pulses in the CARS system of FIG. 1.

FIG. 4 shows the effect of the glass blocks 24, 28 and 30 on pair of Stokes and pump pulses 40 and 42 derived from the same laser pulse. FIG. 4 shows the pulses 40 and 42 in the form in which they enter the microscope 16 for application to the target sample. The glass blocks 24 and 28 are designed to have a cumulative dispersive effect on the Stokes pulse 40 that causes that pulse to undergo a linear chirp of frequency versus time with a particular gradient. The glass blocks 30 and 28 are designed to have a cumulative dispersive effect on the pump pulse 42 that causes that pulse to undergo a linear chirp of frequency versus time with a gradient substantially equal to the gradient of the Stokes pulse chirp. As can be seen in FIG. 4, the lowest frequency components of the Stokes and pump pulses 40 and 42 reach the microscope at the same time. This alignment is achieved by adjusting the position of retroreflector 32 to adjust the travel time of the pump pulse 42 back to the splitter 18 relative to the travel time of the Stokes pulse 40 back to the splitter 18.

FIG. 4 also shows the pulse 44 of CARS light that is emitted by the target sample in response to the Stokes and pump pulses 40 and 42. At all times, the instantaneous frequency difference (IFD) between the Stokes and pump pulses 40 and 42 is constant. The CARS pulse 44 corresponds to a vibrational mode in the target sample whose resonant frequency $\omega_v$ is equal to the IFD. Since the CARS pulse 44 corresponds to a single vibrational mode in the target sample, it suffices to detect the CARS pulse 44 with a simple photomultiplier tube (not shown) within the microscope 16. The microscope 16 also includes a filter (not shown) for rejecting any light emanating from the sample whose frequency falls within the bandwidth of the laser 14.

Figure 5:
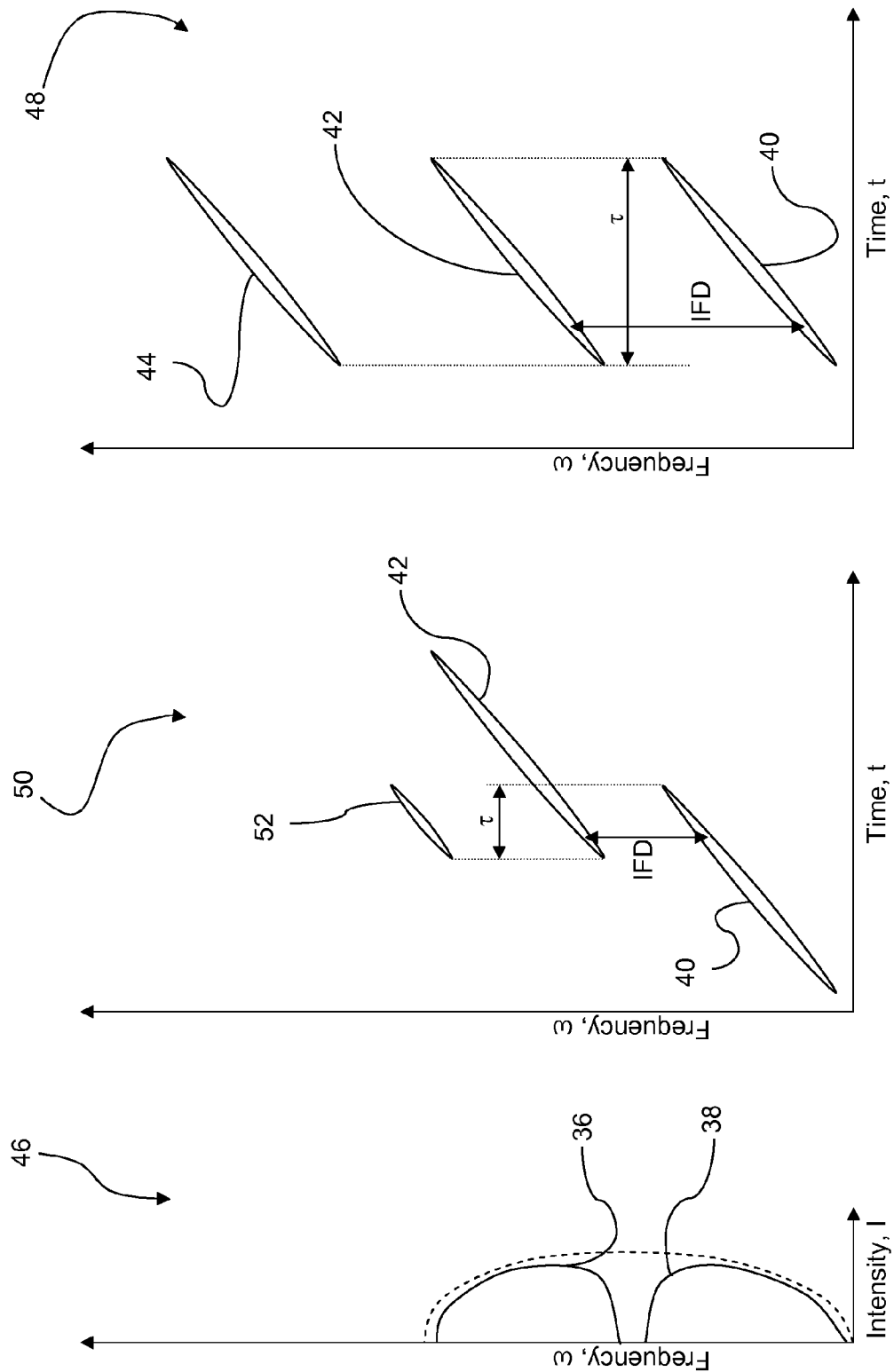
FIG. 5 is provides various graphs relating to pulses within the CARS system of FIG. 1 under operating parameters different to those pertaining in FIG. 4.

FIG. 5 illustrates the effect of varying the travel time of the pump beam 22 using the motor 34. For ease of reference, FIG. 5 includes a reproduction, indicated 46, of the spectrum of FIG. 3 and a reproduction, indicated 48 of the graph of FIG. 4. In graph 48, the timing relationship of the Stokes and pump pulses 40 and 42 is indicated by τ, which is a measure of time elapsing between the arrival at the microscope 16 of the low frequency end of chirped pump pulse 42 and the arrival of the high frequency end of the Stokes pulse 40. The IFD is also shown in graph 48. The graph indicated 50 shows the effect of reducing τ by moving the retroreflector 32. With τ reduced, it is apparent that the IFD is still constant but has a lower value. The CARS pulse that is produced in this situation is indicated 52.

Thus, the retroreflector 32 can be moved backward or forwards along the path of the pump beam 22 as necessary to tune the IFD to correspond to the resonant frequency $\omega_v$ of a vibrational mode within the target sample that the user wishes to investigate. The selection of the desired resonant frequency $\omega_v$ is achieved relatively easily by operating the motor 34 and the use of a retroreflector 32 prevents minor irregularities in the motion imposed by the motor 34 from causing misalignment of the light beams.

Figure 6:
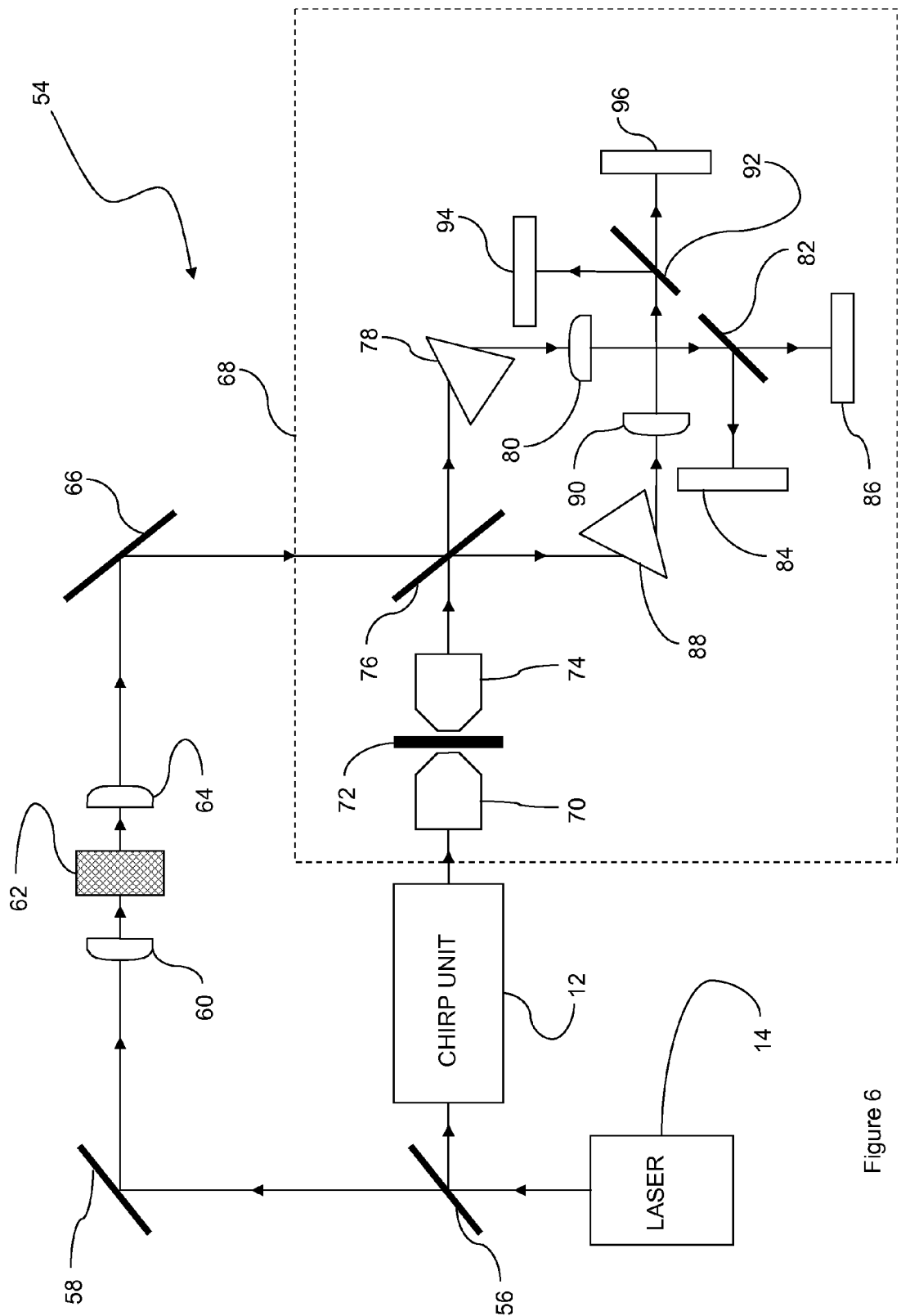
FIG. 6 is a block diagram schematically illustrating a variant of the CARS system of FIG. 1.

FIG. 6 illustrates a CARS system 54 that is a variant of CARS system 10 of FIG. 1. Elements in FIG. 6 that have been carried over from FIG. 1 retain the same reference numerals and their nature and purpose will not be described again in detail. A beam splitter 56 diverts part of the output of the laser 14 away from the chirp unit 12 to form a beam that is reflected from a mirror 58 and then focussed by a lens 60 into a small volume within non-linear element 62 such as a sapphire plate or a high refractive index liquid. Light emerging from the focal volume within the non-linear element 62 results from a third-order mixing process within the non-linear element 62 (e.g. the optical Kerr effect). Light emerging from the focal volume within the non-linear element 62 is then focussed back into a beam by lens 64. The beam from lens 64 is then reflected from mirror 66 and into microscope 68 as a reference beam.

The microscope 68 includes an objective lens 70 for focussing the Stokes and pump pulses from the chirp unit 12 into a volume within the sample 72. A further objective lens 74 collects CARS pulse light from the targeted volume within the sample 72 and projects it as a beam onto a beam splitter 76. Also incident upon beam splitter 76 is the reference beam from the non-linear element 62.

Some (ideally half) of the light from the objective lens 74 is transmitted through the beam splitter 76 to a prism 78 and some of the light from the reference beam is reflected from the beam splitter 76 to the prism 78. The beam emerging from the prism 78 is focussed by a lens 80 and is divided into two orthogonally polarised components by polarising beam splitter 82. The polarised components are then detected by respective line scan cameras 84 and 86 lying in the image plane of the lens 80. The prism 78 creates a wavelength dispersion in the light received from the beam splitter 76 and the lens 80 translates the wavelength dispersion into a range of positions along each of the line scan cameras 84 and 86.

Some (ideally half) of the light from objective lens 74 is reflected by the beam splitter 76 to a prism 88 and some of the light from the reference beam is transmitted through the beam splitter 76 to the prism 88. The beam emerging from the prism 88 is focussed by a lens 90 and is divided into two orthogonally polarised components by polarising beam splitter 92. The polarised components are then detected by respective line scan cameras 94 and 96 lying in the image plane of the lens 90. The prism 88 creates a wavelength dispersion in the light received from the beam splitter 76 and the lens 90 translates the wavelength dispersion into a range of positions along each of the line scan cameras 94 and 96. The polarised components travelling to line scan cameras 86 and 96 have parallel polarisations.

The interference between CARS light and reference beam creates a spectral intensity interference pattern on each line scan camera 84, 86 94 and 96. The images from a pair of cameras receiving the same polarisation (e.g. cameras 84 and 94) are subtracted from one another to isolate the interference pattern (spectral interferogram) for that polarisation, and to eliminate the individual spectra of the CARS light and reference beam (the individual spectra of the CARS light and the reference beam can be detected on the line scan cameras 84, 86, 94 and 96 by blocking the unwanted one of the reference beam or the CARS light). From the spectral interferogram, the spectral amplitude and phase of the CARS light can be retrieved by spectral interferometry (J. Opt. Soc. Am. B 12, 2467 (1995)). For this, we have to adjust the arrival time (by the optical path length) of a pulse in the reference beam to be before the corresponding CARS pulse such that there is no significant temporal overlap between the reference pulse and the CARS signal. (Typically, we would use about 0.5 ps between the reference pulse and the beginning of the corresponding CARS pulse in the system shown in FIG. 6. Choosing a much shorter value results in overlap, and choosing a much longer value reduces the temporal range over which the CARS can be retrieved from the interferogram for a given spectral resolution.) Thus, the microscope 68 is able to recover amplitude and phase information for the CARS light from the target volume within the sample 72. This ability enables more sophisticated measurements to be made when certain adjustments are made to the chirp unit 12, as will now be explained.

Figure 7:
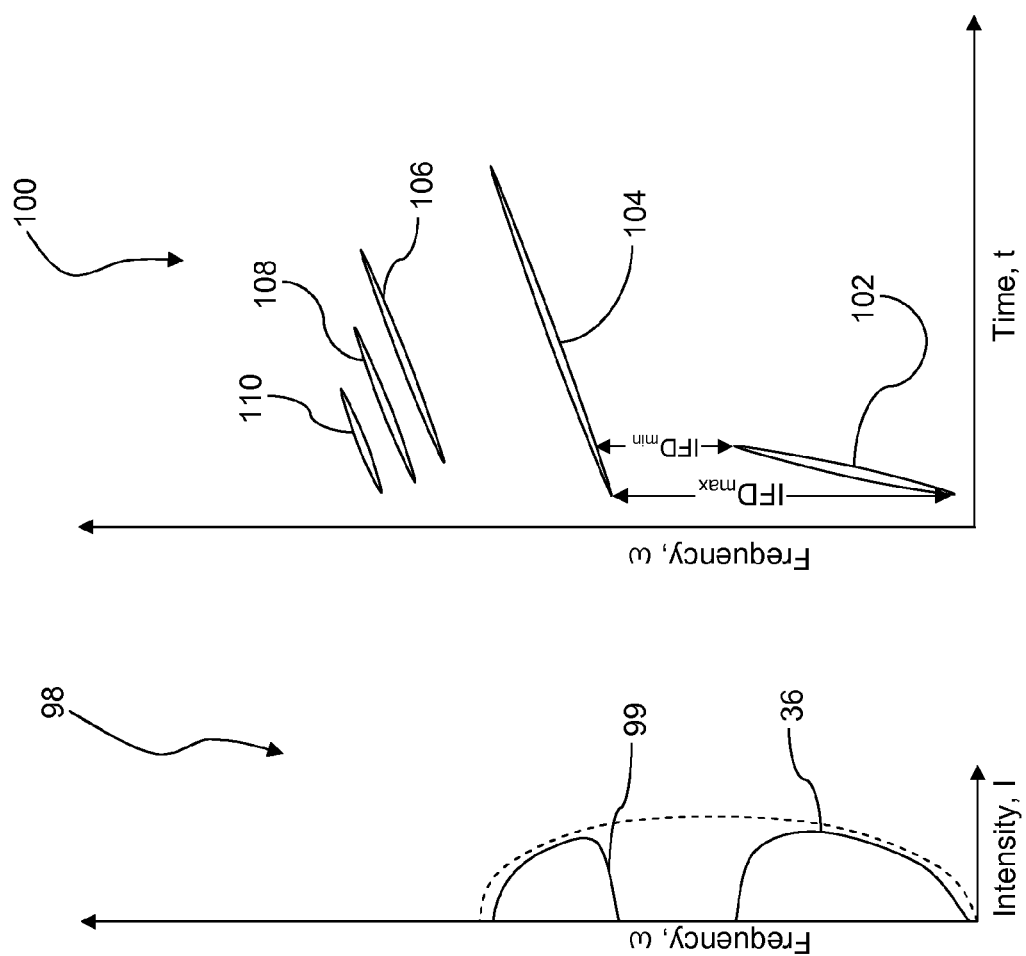
FIG. 7 is a graph of intensity versus time for various pulses in the CARS system of FIG. 6.

Specifically, the glass blocks 24, 28 and 30 are redesigned such that, although both the Stokes and pump beams are still given linear chirps, the rate of change of frequency of a Stokes beam pulse is now very different to the rate of change of frequency of a pump beam pulse. The Stokes beam pulses are chirped only slightly, in order to reduce the peak power applied to the sample material. On the other hand, the pump beam pulses are strongly chirped such that the frequencies in a pump beam pulse arrive at the sample over a relatively long period of time, comparable to the vibrational dephasing times. The effect of these changes to the chirp unit 12 is illustrated in FIG. 7. In addition, that diagram illustrates the option of redesigning the dichroic beam splitter 18 to use a smaller frequency sub-band for the pump beam than previously. This sub-band is located at the upper end of the band of output frequencies of the laser 14 such that a relatively large central sub-band of the band of output frequencies of the laser 14 is not used to illuminate the sample in the microscope 16. This reduces the power to which the sample material is exposed and therefore reduces the risk of damaging the sample material.

FIG. 7 shows in graph 98 the sub-bands of the output band of the laser 14 that are now used for the Stokes and pump beams. The dashed line represents, as in FIG. 3, the band of output frequencies of the laser 14. The adjusted sub-band that is allocated to the pump beam is indicated 99. It will be apparent that the gap between sub-band 99 and the sub-band 36 that is used for the Stokes beam is now wider than the gap between sub-bands 38 and 36 in FIG. 3, representing a reduction in the power that is applied to the sample achieved through the optional redesign of the dichroic beam splitter 18. FIG. 7 also provides a graph 100 illustrating the modified forms now taken by a Stokes pulse 102 and a pump pulse 104 derived from the same pulse from the laser 14.

With the retroreflector 32 positioned such that the Stokes and pump pulses 102 and 104 begin to arrive at the same time, it is apparent that, over the duration of the Stokes pulse 102, the IFD varies over a range from a maximum value, $IFD_{max}$, to a minimum value, $IFD_{min}$. Since the IFD varies over a range, the pump and Stokes pulses can therefore excite CARS light from different vibrational modes of the sample material having different resonant frequencies in the range between $IFD_{max}$ and $IFD_{min}$. Thus, CARS light produced in response to pulses 102 and 104 consists of a collection of CARS pulses 106 to 110 that each relate to a different resonant frequency of the sample material. Each of the CARS pulses 106 to 110 endures for a period of time determined by the coherence time of its vibrational mode. The vibrational coherence time decreases from pulse 106 to pulse 108 to pulse 110.

Figure 8:
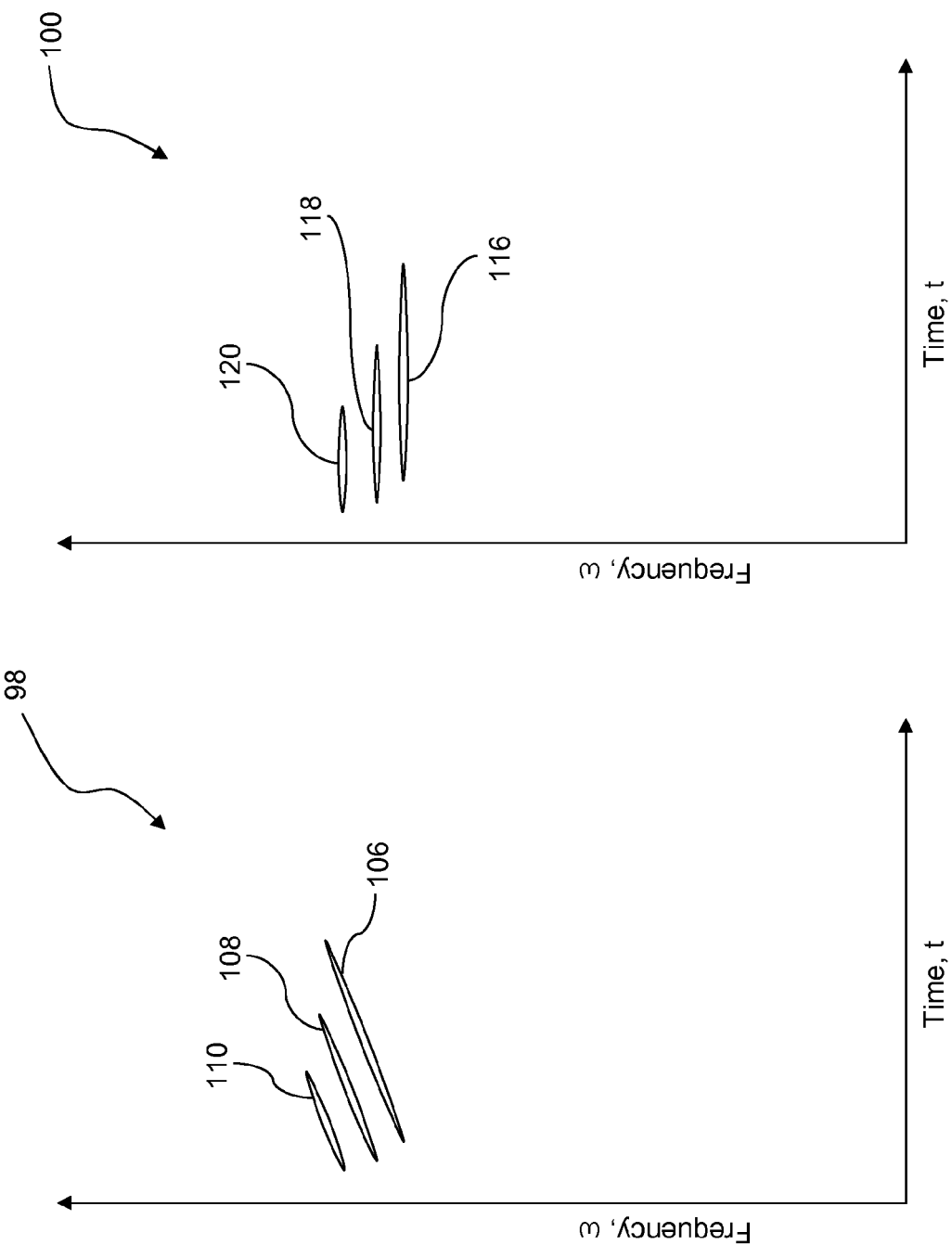
FIG. 8 shows two graphs of pulses of CARS light, before and after compensation, respectively.

The CARS light gathered by objective 74 in response to Stokes pulse 102 and pump pulse 104 is shown again in graph 112 in FIG. 8. Since the microscope 68 detects the CARS light in terms of its amplitude and phase, mathematical techniques such as those described in OPTICS LETTERS 31, 1543 (2006) can be applied to mathematical data representing the CARS light detected by the microscope 68 in order to flatten the slopes of pulses 106 to 110 that are due to the chirping of the pump pulse 104. This recovers a spectrum as shown in graph 114 in which the different vibrational modes that have been excited within the sample can be distinguished: pulses 106 to 110 have been flattened into pulses 116 to 120, respectively. Specifically, the spectral of the temporal CARS response can be retrieved in amplitude and phase, which can be used to retrieve the chemical composition by linear decomposition, as opposed to measuring the CARS intensity only.

Figure 9:
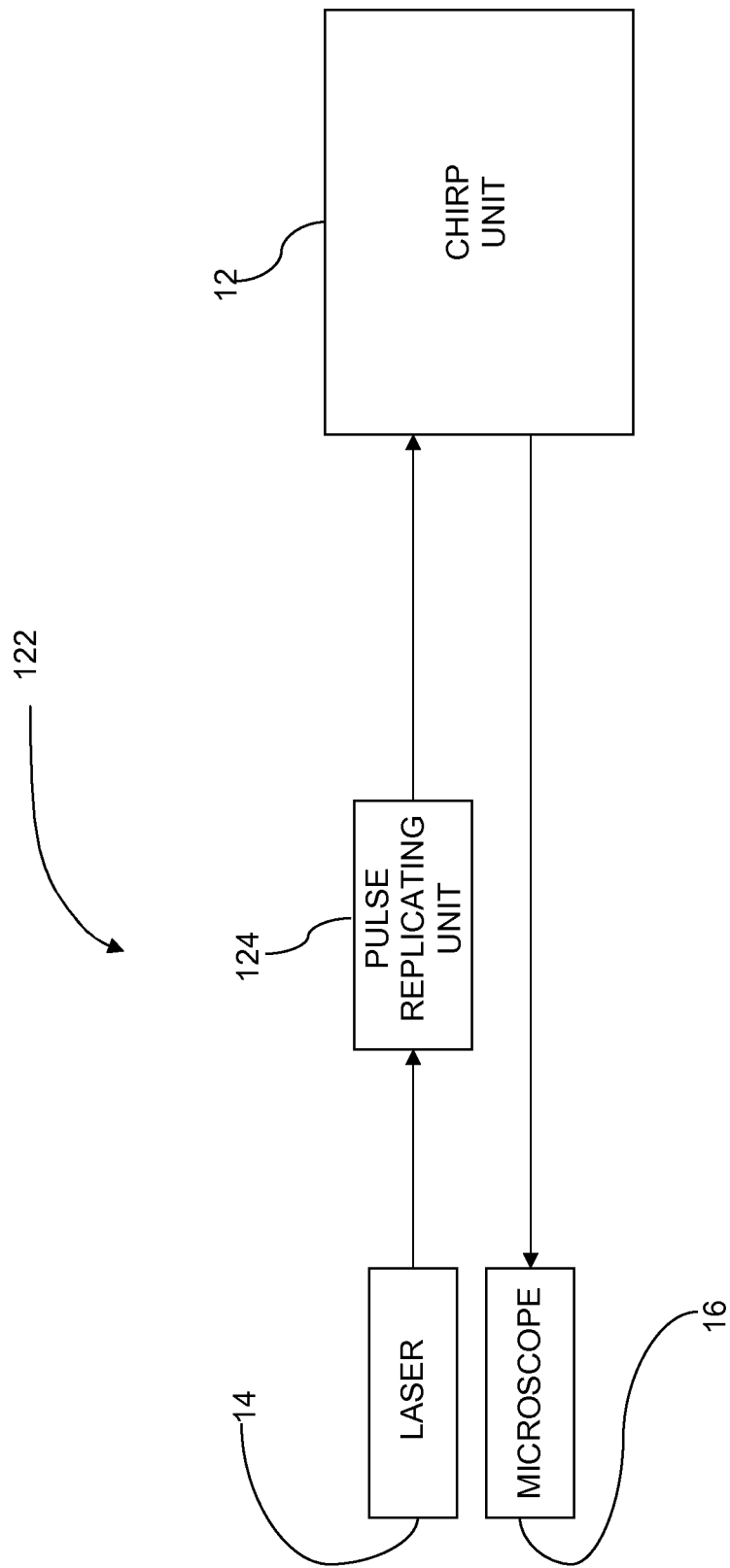
FIG. 9 is a block diagram schematically illustrating a variant of the CARS system of FIG. 6.

Another CARS system 122 is shown in FIG. 9. CARS system 122 is a variant of CARS system 10 in which a pulse replicating unit 124 has been inserted between the laser 14 and the chirp unit 12. The pulse replicating unit 124 is shown in greater detail in FIG. 10.

Figure 10:
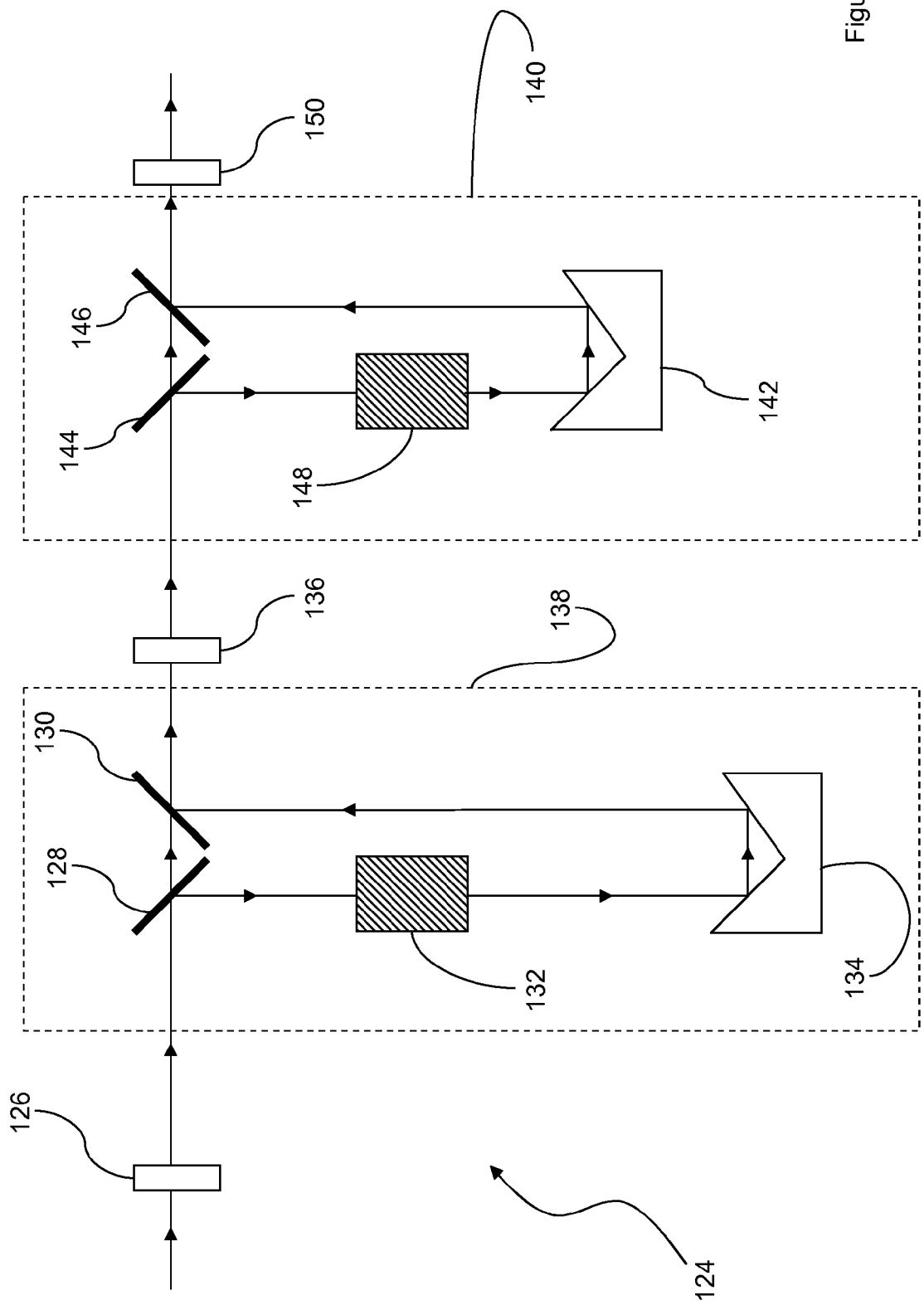
FIG. 10 is a block diagram schematically illustrating the pulse replicating unit within the CARS system of FIG. 9.

As shown in FIG. 10, the beam from the laser 14 enters the pulse replicating unit 124 and passes through a half wave plate 126. The laser beam then proceeds to a polarising beam splitter 128 which splits the laser beam into orthogonally polarised components. One of these components is a "transmitted component" that is transmitted through the polarising beam splitter 128 to a second polarising beam splitter 130. The other component is a "reflected component" that is reflected through a dispersive glass block 132 and is then reflected by a mirror pair 134 to the second polarising beam splitter 130. The half-wave plate 126 is orientated to rotate the linear polarization of the input laser beam to give desired relative intensities to the transmitted and reflected components produced by the polarizing beam splitter 128. The second polarising beam splitter is orientated to transmit the transmitted component and to reflect the reflected component to travel in the same direction. The recombined polarisations of the laser beam then travel from the polarising beam splitter 130 to a half wave plate 136. The polarising beam splitters 128 and 130, the glass block 132 and the mirror pair 134 constitute a first delay arm 138 that delays the reflected component of the laser beam by an amount $T_1$ relative to the transmitted component of the laser beam. Moreover, the reflected component undergoes dispersion in the delay arm 138 by an extent determined by the properties of the glass block 132, and the effects of this dispersion will be described later.

From the half wave plate 136, the laser beam proceeds through a further delay arm 140 having a construction analogous to that of arm 138. The half wave plate 136 is orientated to give desired relative intensities to the orthogonally polarised components produced by polarising beam splitter 144. Delay arm 140 imposes a delay of $T_2$ on the component of the laser beam that travels to mirror pair 142 relative to the component that travels straight through polarising beam splitters 144 and 146. Moreover, the component of the laser beam that travels through glass block 148 undergoes additional dispersion. After the second delay arm 140, the laser beam travels through a quarter wave plate 150 and then into the chirping unit 12.

The laser 14 emits pulses. FIGS. 11a to 11h show the effect of the pulse replicating unit 124 on an arbitrary pulse from the laser 14. Each of FIGS. 11a to 11h provides a pair of graphs of intensity versus time. The upper graph in each pair shows intensity in the polarisation parallel to that of the reflected component produced by polarising beam splitter 128 and the lower graph in each pair shows intensity in the orthogonal polarisation parallel to the transmitted component of polarising beam splitter 128. The two orthogonal polarisations shown in FIGS. 11a to 11h shall henceforth be referred to as the "reference polarisations". In each of FIGS. 11a to 11h, the time axes of the upper and lower graphs are aligned to some common zero time. For ease of description, it is further assumed that the polarisations of the transmitted components of polarising beam splitters 128 and 144 are parallel and that the polarisations of the reflected components produced by polarising beam splitters 128 and 144 are parallel.

Figure 11A:
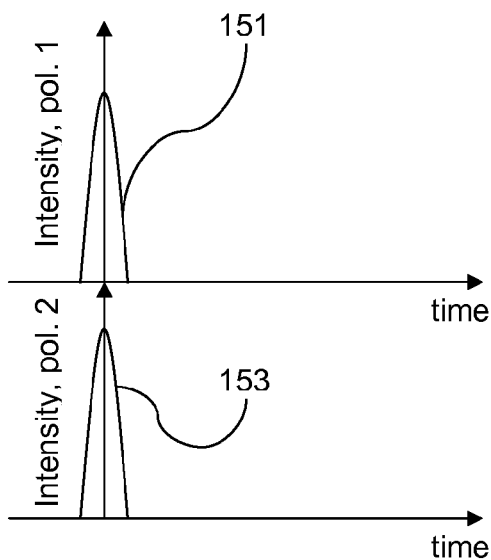
FIGS. 11a to 11h are graphs showing the polarisation of pulses within the pulse replicating unit of FIG. 10.
Figure 11B:
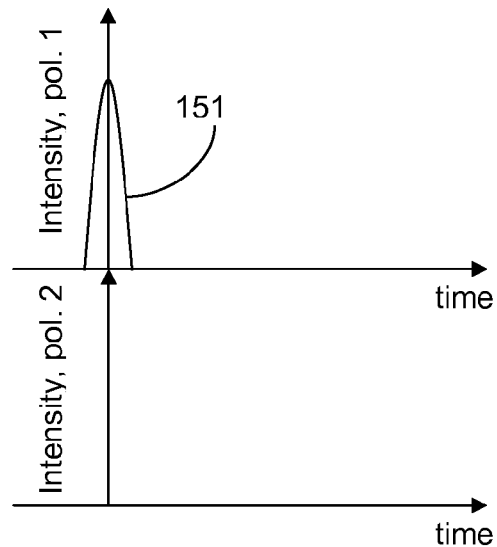
Figure 11C:
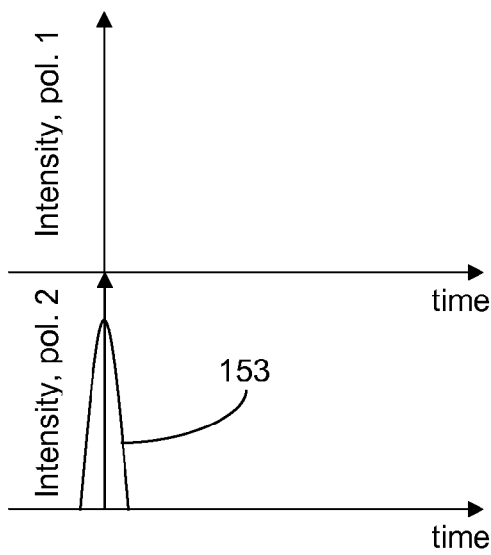
Figure 11D:
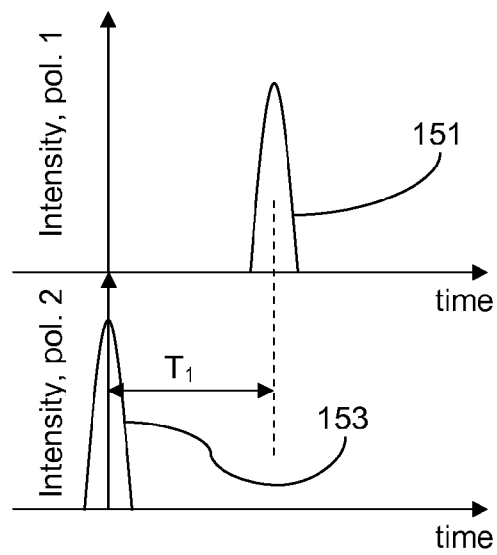

FIG. 11a shows the output of the half wave plate 126 in response to an arbitrary pulse from the laser 14. The half wave plate 126 is positioned to rotate the linear polarisation of the arriving laser pulse so that its intensity is split equally between the reference polarisations giving orthogonally polarised pulses 151 and 153. FIG. 11b shows the output of polarising beam splitter 128 towards block 132, i.e. just pulse 151. FIG. 11c shows the output of polarising beam splitter 128 towards splitter 130, i.e. just pulse 153. FIG. 11d shows the output of polarising beam splitter 130, i.e. pulse 153 and, a time $T_1$ later, pulse 151.

Figure 11E:
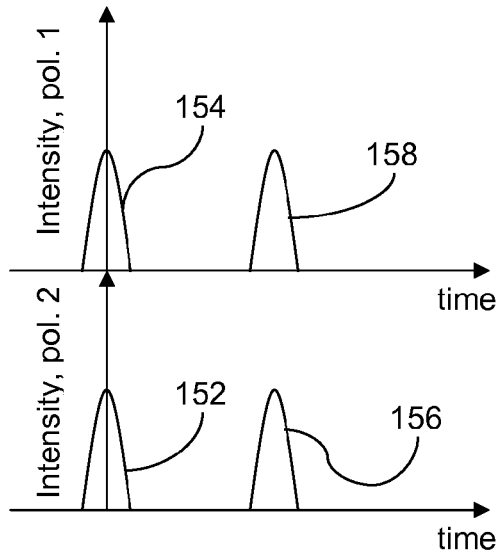
Figure 11F:
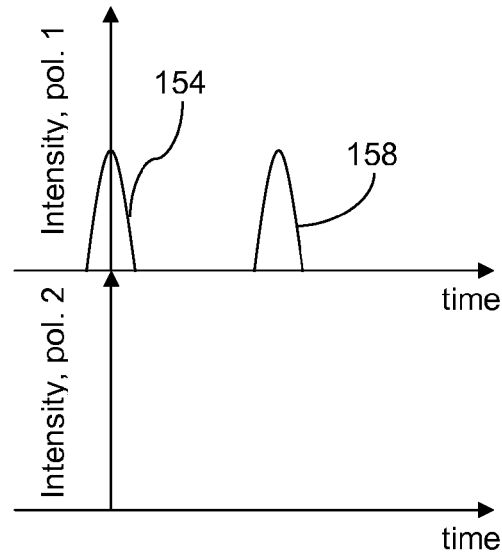
Figure 11G:
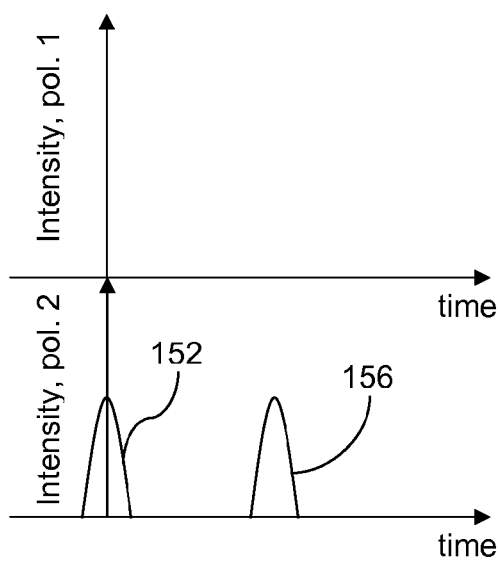
Figure 11H:
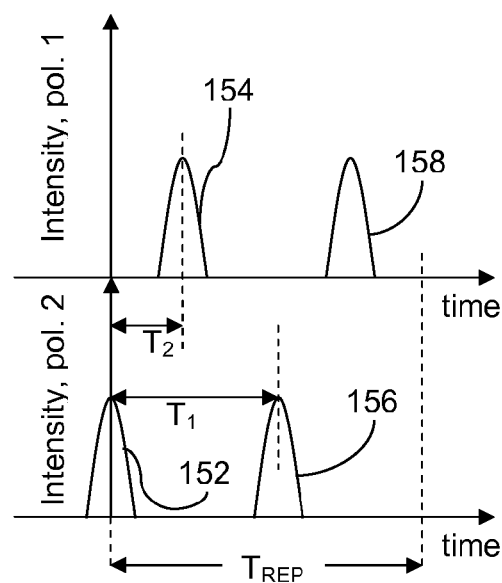

The light from polarising beam splitter 130 travels towards half wave plate 136. The half wave plate 136 is angled so as to divide pulse 153 equally between the reference polarisations to create pulses 152 and 154, as shown in FIG. 11e. Likewise, delayed pulse 151 is divided equally into pulses 158 and 156, again as shown in FIG. 11e. FIG. 11f shows the output of polarising beam splitter 144 towards block 148, i.e. just pulses 154 and 158. FIG. 11g shows the output of polarising beam splitter 144 towards splitter 146, i.e. just pulses 152 and 156. FIG. 11h shows the output of polarising beam splitter 146, i.e. pulses 152 and 156 and, delayed by a time $T_2$, pulses 154 and 158. The delays $T_1$ and $T_2$ are constrained such that all four pulses fall within a pulse repetition period $T_{REP}$ of the laser 14 ($1/T_{REP}$ being the rate at which the laser emits pulses).

The quarter wave plate 150 converts the linear polarisations of pulses 152 to 158 into circular polarisations so that, when pulses 152 to 158 are applied to a sample, the CARS response that they elicit, when time-averaged, is independent of the specific orientation between the polarisation of the pulses and the structure of the sample.

In order to keep FIGS. 11a to 11h simple, no attempt has been made to show the dispersive effect of blocks 132 and 148 in those Figures. However, FIG. 12 shows not only the effect of that dispersion but also the effect of dichroic beam splitter 18 in the chirp unit 12 on the pulses 152 to 158. Accordingly, FIG. 12 shows pulse 152 split by the dichroic beam splitter 18 into a Stokes pulse 152a and a pump pulse 152b. Likewise, pulses 154 to 158 are split into respective Stokes pulses 154a to 158a and respective pump pulses 154b to 158b.

Pulse 154 has been dispersed by glass block 148 and therefore "leans forward" in FIG. 12, as indicated by the dashed line connecting pulses 154a and 154b. As a result of this dispersion, the onset of the pump pulse 154b is delayed slightly with respect to the onset of the Stokes pulse 154a. This delay alters the size of parameter τ (see FIG. 5 and the corresponding description) and hence the IFD that pulses 154a and b would otherwise target according to the current position of adjustable retroreflector 32 and the dispersion introduced by glass blocks 24, 28 and 30. In other words, the delay between the start of Stokes pulse 154a and the start of pump pulse 154b adjusts the resonant frequency $\omega_v$ that pulse 154 targets.

Likewise, the start of pump pulse 156b is delayed with respect to the start of Stokes pulse 156a by the dispersion of glass block 132 and the start of pump pulse 158b is delayed with respect to the start of Stokes pulse 158a by the dispersion of glass blocks 132 and 148. Accordingly, all four pulses 152 to 158, due to their differing degrees of dispersion, target different resonant frequencies in the sample. The chirping of the pulses 152a to 158b by the glass blocks 24, 28 and 30 and the delaying effect of the path difference in the routes to mirrors 26 and 32 is not illustrated in FIG. 12 in order to avoid complicating the diagram. However, the repetition period $T_{REP}$ of the pulses from the laser 14 is again shown in FIG. 12.

As mentioned earlier, the microscope 16 detects CARS pulses from the sample using a photomultiplier which transduces the intensity of the received CARS light into an electrical signal, I(t). Each of 152 to 158 can produce a corresponding pulse of CARS light and these CARS pulses are short compared to the time resolution of this photomultiplier such that the CARS pulses can be considered instantaneous in the electrical signal I(t) Therefore, ignoring noise and the like, the signal I(t) has the form of a series of delta functions that repeats every $T_{REP}$. The signal I(t) can therefore be expressed as a Fourier series:

$$I(t) = \frac{a_0}{2} + \sum_{i=1}^{\infty} (a_i \cos\omega_i t + b_i \sin\omega_i t)$$

where:

$$\omega_i = \frac{2\pi}{T_{REP}} i$$

$$a_i = \frac{2}{T_{REP}} \int_0^{T_{REP}} I(t)\cos\omega_i t \cdot dt$$

$$b_i = \frac{2}{T_{REP}} \int_0^{T_{REP}} I(t)\sin\omega_i t \cdot dt$$

The delay arms 138 and 140 are designed such that $2T_1 = 4T_2 = T_{REP}$. As a result, the set of delta functions that repeats within a period of I(t) of duration $T_{REP}$ is:

$$I(t) = \sum_{n=1}^{4} T_{REP} A_n \delta\left(t - \frac{(n-1)T_{REP}}{4}\right)$$

where $A_1$ to $A_4$ are the time-averaged signals of (the seemingly instantaneous) CARS pulses that are triggered by pulses 152 to 158, respectively. It can be shown mathematically that:

$$\frac{a_0}{2} = A_1 + A_2 + A_3 + A_4$$

$$a_1 = A_1 - A_3$$

$$b_1 = A_2 - A_4$$

$$a_2 = A_1 - A_2 + A_3 - A_4$$

From these four simultaneous equations, the magnitudes $A_1, A_2, A_3$ and $A_4$ of the four CARS pulses 152 to 158 can be recovered.

Figure 13:
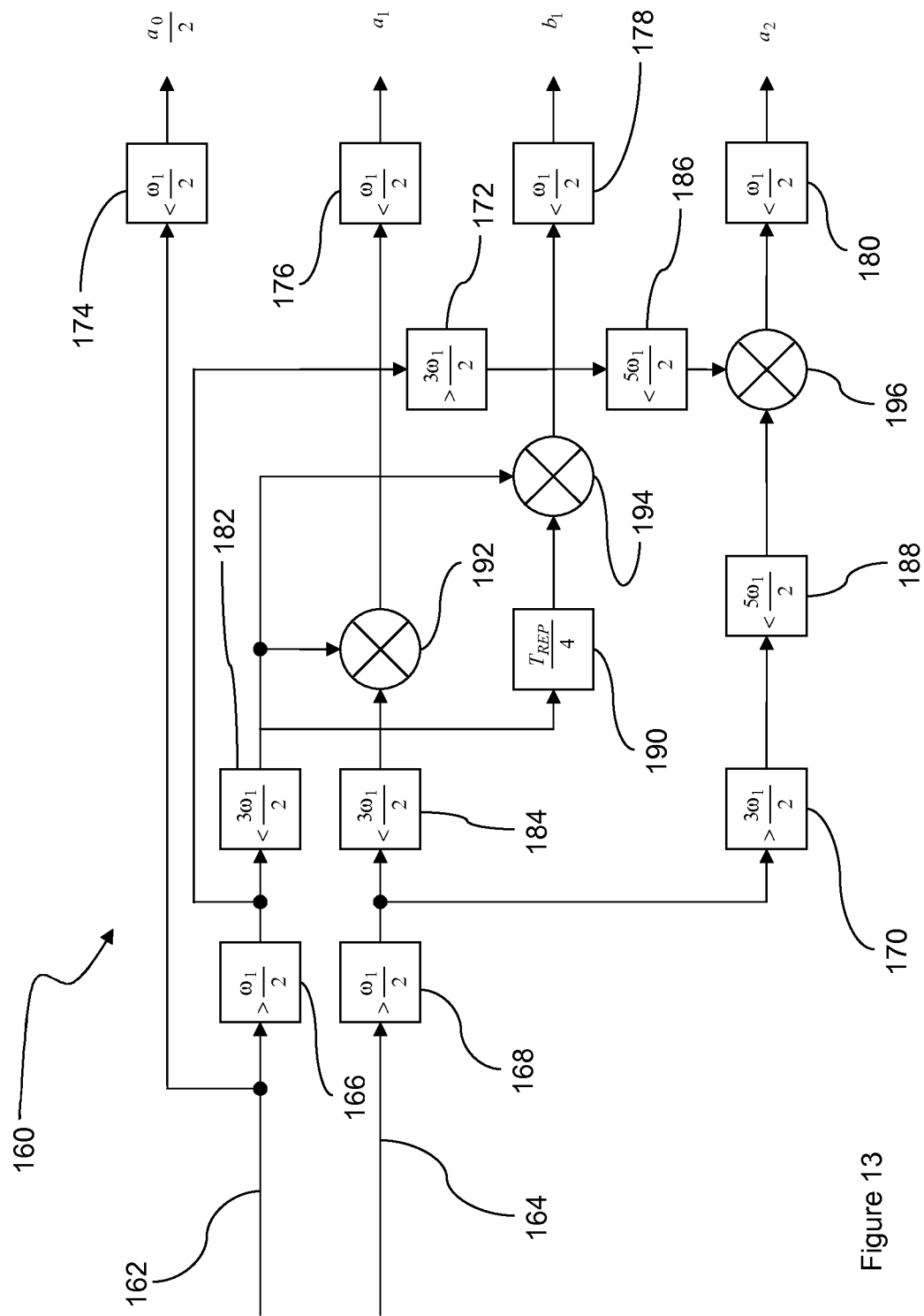
FIG. 13 is a block diagram schematically illustrating a circuit for processing an output signal from a photomultiplier tube in the microscope of the CARS system of FIG. 9.

FIG. 13 shows an electrical circuit 160 within the microscope 16 for processing the photomultiplier signal I(t) to deduce $$\frac{a_0}{2},$$

$a_1$, $b_1$ and $a_2$. The signal I(t) the photomultiplier is applied on input line 162. Input line 164 receives an electrical signal that is derived from a photodiode (not shown) within the laser 14 and which consists of a delta function repeated at the pulsing frequency of the laser 14 (limited by the bandwidth of the photodiode which, just to clarify, is typically about 500 MHz, i.e. $8\omega_1$). The electrical signal applied to line 164 is therefore also a Fourier series of the same frequencies that are contained in I(t).

The circuit 160 contains a number of high pass filters 166 to 172. Filters 166 and 168 block frequencies below $$\frac{\omega_1}{2}$$

(it will be recalled that $$\omega_1 = \frac{2\pi}{T_{REP}}$$

and filters 170 and 172 block frequencies below $$\frac{3\omega_1}{2}.$$

The circuit 160 also contains a number of low pass filters 174 to 188. Filters 174 to 180 block frequencies above $$\frac{\omega_1}{2},$$

filters 182 and 184 block frequencies above $$\frac{3\omega_1}{2}$$

and filters 186 and 188 block frequencies above $$\frac{5\omega_1}{2}.$$

The circuit also includes a delay line 190 for delaying the signal exiting filter 182 by $$\frac{T_{REP}}{4}$$

to phase shift that signal by $$\frac{\pi}{2}$$

radians.

The circuit 160 also includes a number of mixers 192 to 196, each arranged to perform frequency down conversion. The signals supplied to the circuit 160 contain only frequencies that satisfy the relation $k\omega_1$, where k is an integer (including zero). Therefore, the output of mixer 192 contains a d.c. component that is proportional to $a_1$, the output of mixer 194 contains a d.c. component that is proportional to $b_1$ and the output of mixer 196 contains a d.c. component that is proportional to $a_2$. The proportionality constants for $a_1$, $b_1$ and $a_2$ are determined by the losses of mixers 192 to 196 and by the amplitude of the signal on line 164. Thus, the CARS system described with respect to FIGS. 9 to 13 is useful in that various measurements can be time-multiplexed without additional optics. Coefficient $a_1$ is a measure of the difference in size between CARS pulse heights $A_1$ and $A_2$ and can therefore be used in a differential measuring technique, as will now be described.

Consider, for example, the CARS pulse that is produced in response to pulse 152. As explained previously, this CARS pulse will include CARS light from the vibrational mode whose resonant frequency, call it $f_0$, is targeted by the IFD to which pulse 152 corresponds. However, the CARS pulse will also include non-resonant CARS light from all the vibrational modes of the material lying within the focal volume of the microscope 16 that have a resonant frequency of greater than $f_0$, and also from purely electronic contributions. This non-resonant CARS light is a background CARS signal that tends to mask the wanted CARS signal that is the CARS light from the vibrational mode whose resonant frequency is $f_0$.

Since water is a dominant component of biological cells, the background CARS signal from water can dominate or mask the resonant CARS signal that is elicited from a vibrational mode of an aspect of a cell that is under investigation. In order to address this problem, the differential nature of coefficient $a_1$ can be exploited, as follows.

Consider that pulse 152, which, it will be recalled, draws a CARS response of magnitude $A_1$, is given by the chirp unit 12 an IFD of $f_1$ that is the resonant frequency of a vibrational mode of interest within the membrane of a type of cell that is to be studied. Assume also that pulse 154, which, it will be recalled, draws a CARS response of magnitude $A_2$, targets a vibrational mode whose resonant frequency is $f_2 > f_1$ and is not expected to be found in water or in the type of cell being investigated.

First, with the focal volume of the microscope containing only water, the half wave plate 126 is are adjusted to alter the magnitudes of peaks 152 and 156 so that the CARS pulse magnitudes $A_1$ and $A_3$ are substantially equal and $a_1$ (the output signal of filter 176) is substantially zero. In this situation, the CARS pulse magnitudes $A_1$ and $A_2$ are due entirely to non-resonant CARS light. Then, the sample material is located within the focal volume. Any change that results in the output signal of filter 176 is thus attributable to resonant CARS light from the vibrational mode of interest that has a resonant frequency of $f_1$. In other words, the nulling of the output signal of filter 176 by adjusting the half wave plate 126 has the effect of compensating the non-resonant CARS background signal from water when the microscope is used to investigate a real sample. Since all four pulses are derived from the same laser pulse, they do not exhibit equal classical intensity fluctuations, which are completely suppressed in the balanced signal $a_1$, which can therefore be limited only by the shot-noise of the signal. This enables a sensitive detection of small changes in material composition. A similar argument holds for the coefficients $a_{2,3}$, so that in total three balanced signals are extracted.

With the glass blocks 132 and 148 removed (such that pulses 152 to 158 are all given the same IFD by the chirp unit 12), the CARS system 122 can be adapted to perform some other measurements, as will now be explained.

The beam directions of the four pulses 152 to 158 can all be made slightly different by the tip/tilt of beam splitters 146 and 130 Then, the microscope will focus the pulses into laterally displaced focal volumes within the sample. Thus, the CARS pulses produced in response to pulses 152 to 158 relate to different locations within the sample. Using a lateral displacement comparable to the size of the focal volume, the coefficient $a_1$, represents a spatial gradient in the CARS response within the sample (since $A_1$ and $A_3$ now relate to different locations within the sample). Similar arguments hold for $a_{2,3}$.

It is also possible to remove the quarter wave plate 150 and replace it with a half wave plate. Under these circumstances, the pulses 152 and 156 emerge from the pulse replicating unit 124 with a first polarisation and pulses 154 and 158 emerge with a second, orthogonal, polarisation. It will be recalled that the CARS pulses elicited by pulses 152 to 158 have magnitudes $A_1$ to $A_4$, respectively. Therefore, coefficient $a_2=A_1-A_2+A_3-A_4$ is a measure of the difference of the CARS responses of the sample to first and second polarisations of the pulses 152 to 158. Thus, it is possible to probe the spatial ordering of the sample material leading to birefringence in the CARS light, as in e.g. in Lipid membranes (see J. Raman Spectrosc. 34, 642-650 (2003)). The additional half wave plate can of course be rotated to rotate the two orthogonal polarisations of the pulses 152 to 158 relative to the sample material.

Various modifications of the described CARS systems will be apparent to readers skilled in the art. For example:
- non-polarising beam splitters could be used in the pulse replicating unit 124 (although a loss of intensity would occur when recombining the beams at the output of each of the delay arms 138 and 140).
- polarising beam splitters 82 and 92 could be omitted with the light from lenses 80 and 90 being focussed on to respective single line scan cameras (although polarisation information about the CARS light would be lost)
- a single camera with two lines could be used together with a polarization displacer instead of 82 and 92.
- both outputs of beam splitter 76 could be guided over a single dispersing beam path, using a line scan camera with 2 lines (without polarization displacer) or 4 lines (with polarization displacer)
- Prisms 78, 88 could be exchanged with gratings
- the number of, and disposition of the delayed pulses that the pulse replicating unit 124 manufactures within the laser's pulse repetition period $T_{REP}$ could be altered (with concomitant adjustments to circuit 160). This can be done without loss of laser power by changing the number of delay units 138, 140. A total number of $2^n$ pulses and respective electrical signals are produced for n replica.
- the reference beam incident upon beam splitter 76 could be provided directly from laser 14 (depending on the nature of the laser) thus removing the need for non-linear element 62 and lenses 60,64.

The invention claimed is:

1. An apparatus for studying a sample, the apparatus comprising:
   a light source emitting pulsed light;
   at least one beam splitter arranged to convert a pulse of light from the source into a plurality of derived light pulses distributed in time;
   a filter arranged to separate each derived light pulse into:
      a first interrogation pulse traveling on a first path consisting of a subset of the derived light pulse's frequencies; and
      a second interrogation pulse traveling on a second path and consisting of another subset of the derived light pulse's-frequencies;
   a frequency disperser arranged to change each derived light pulse's first and second interrogation pulses into respective first and second chirped pulses by dispersing in time the frequencies within the first and second interrogation pulses;
   a plurality of optical paths arranged to:
      convey each derived light pulse's first and second chirped pulses; and
      apply each derived light pulse's first and second chirped pulses to the sample in time overlap; and
   a detector for detecting stimulated light that is stimulated from the sample by the interaction of each derived light pulse's first and second chirped pulses.

2. The apparatus according to claim 1, wherein the frequency disperser is arranged to introduce into each derived light pulse's first interrogation pulse a first substantially linear dispersion over at least a band of frequencies therein and is arranged to introduce into each derived light pulse's second interrogation pulse a second substantially linear dispersion over at least a band of frequencies therein.

3. The apparatus according to claim 2, wherein the first and second linear dispersions have substantially the same rate of change of delay with frequency.

4. The apparatus according to claim 3, wherein the detector produces a signal recording the detected stimulated light over time and the apparatus further comprises a calculator for calculating at least one quantity, the at least one quantity being at least indicative of a respective coefficient of a Fourier series representing the signal.

5. The apparatus according to claim 1, wherein the at least one beam splitter comprises at least one partially transmissive mirror arranged to divide the pulse from the source into parts that travel along paths of different lengths to reach the sample.

6. The apparatus according to claim 1, further comprising a deflector for creating a difference in the direction of travel between first and second derived light pulses such that the first and second chirped pulses of the first derived light pulse stimulate light from a first location within the sample and the first and second chirped pulses of the second derived light pulse stimulate light from a different location within the sample.

7. The apparatus according to claim 1, wherein the plurality of optical paths includes an adjusting unit for making a common adjustment to the period between the arrival at the sample of the starts of the first and second chirped pulses, for all of said derived light pulses.

8. The apparatus according to claim 1, wherein the frequency disperser comprises dispersive glass in the paths traversed by the first and second interrogation pulses.

9. The apparatus according to claim 1, wherein the detector is arranged to detect the light stimulated from the sample in terms of its amplitude and phase.

10. The apparatus according to claim 9, wherein the detector further comprises a processor arranged to deduce, from a record of the light stimulated from the sample in terms of its amplitude and phase, a spectrum of the light stimulated from the sample.

11. The apparatus according to claim 1, wherein the light source comprises a pulsed broadband laser.

12. The apparatus according to claim 1, wherein the detector comprises a discriminating device for discriminating CARS light in said light that is stimulated from the sample.

13. The apparatus according to claim 1, wherein the detector is arranged to discriminate light stimulated from the sample in a given linear polarization.

14. A method of studying a sample, the method comprising:
- providing pulsed light from a source;
- converting a pulse of light from the source into a plurality of derived light pulses distributed in time;
- separating each derived light pulse into a first interrogation pulse consisting of a subset of the derived light pulse's frequencies and a second interrogation pulse consisting of another subset of those frequencies;
- chirping the first and second interrogation pulses of each derived light pulse;
- applying each derived light pulse's chirped first and second interrogation pulses to the sample in time overlap; and
- detecting stimulated light that is stimulated from the sample by the interaction of each derived light pulse's chirped first and second interrogation pulses.

* * * * *